United States Patent
Mizutani

(10) Patent No.: US 11,615,686 B2
(45) Date of Patent: *Mar. 28, 2023

(54) MONITORING SUPPORT APPARATUS AND MONITORING SUPPORT METHOD FOR SUPPORTING WORK OF MONITORING PERSON WHO MONITORS PLURALITY OF SUBJECTS BY SEQUENTIALLY VISITING THE PLURALITY OF SUBJECTS

(71) Applicant: PANASONIC INTELLECTUAL PROPERTY MANAGEMENT CO., LTD., Osaka (JP)

(72) Inventor: Kenji Mizutani, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/542,811

(22) Filed: Dec. 6, 2021

(65) Prior Publication Data

US 2022/0092959 A1    Mar. 24, 2022

Related U.S. Application Data

(63) Continuation of application No. 17/000,431, filed on Aug. 24, 2020, now Pat. No. 11,227,475, which is a
(Continued)

(30) Foreign Application Priority Data

May 30, 2018  (JP) .............................. JP2018-104066
Mar. 27, 2019 (JP) .............................. JP2019-061402

(51) Int. Cl.
*G08B 21/02* (2006.01)
*G01S 13/50* (2006.01)
(Continued)

(52) U.S. Cl.
CPC .............. *G08B 21/02* (2013.01); *G01S 13/50* (2013.01); *G01S 13/88* (2013.01); *G08B 5/222* (2013.01); *G08B 27/005* (2013.01); *G16H 40/20* (2018.01)

(58) Field of Classification Search
CPC ...... G08B 21/02; G08B 5/222; G08B 27/005; G01S 13/50; G01S 13/88; G01S 13/42; G16H 40/20
See application file for complete search history.

(56) References Cited

U.S. PATENT DOCUMENTS

| 7,242,306 B2 | 7/2007 | Wildman et al. |
| 8,564,445 B2 * | 10/2013 | Dring ..................... A61B 5/447 600/595 |
| 9,384,651 B2 | 7/2016 | Hsu et al. |

(Continued)

FOREIGN PATENT DOCUMENTS

| JP | 4977806 | 7/2012 |
| JP | 2016-214876 | 12/2016 |
| WO | 2016/151966 | 9/2016 |

OTHER PUBLICATIONS

International Search Report of PCT application No. PCT/JP2019/018317 dated Jul. 9, 2019.

*Primary Examiner* — John A Tweel, Jr.
(74) *Attorney, Agent, or Firm* — Greenblum & Bernstein, P.L.C.

(57) ABSTRACT

An apparatus includes a measuring device, a position specifying circuit, and a determining circuit. The measuring device measures a plurality of subjects by radiating a detecting wave toward the plurality of subjects. The position specifying circuit specifies positions of the plurality of subjects on a basis of information obtained by the measuring device. The determining circuit determines at least one of: a next subject suitable as a subject to be visited next by a
(Continued)

monitoring person among the plurality of subjects; and a movement path along which the monitoring person moves from a position of the monitoring person to the next subject on a basis of the positions of the plurality of subjects specified by the position specifying circuit. A method performs the operations of the measuring device, and the circuits.

19 Claims, 19 Drawing Sheets

Related U.S. Application Data continuation of application No. PCT/JP2019/018317, filed on May 8, 2019.

(51) Int. Cl.
| | |
|---|---|
| *G08B 5/22* | (2006.01) |
| *G16H 40/20* | (2018.01) |
| *G01S 13/88* | (2006.01) |
| *G08B 27/00* | (2006.01) |

(56) References Cited

U.S. PATENT DOCUMENTS

| | | | | |
|---|---|---|---|---|
| 11,160,508 | B2* | 11/2021 | Akatsu | A61B 5/1102 |
| 11,227,475 | B2* | 1/2022 | Mizutani | G16H 40/20 |
| 2002/0183979 | A1* | 12/2002 | Wildman | G07C 9/28 |
| | | | | 702/188 |
| 2012/0293359 | A1 | 11/2012 | Fukuda et al. | |
| 2015/0198709 | A1 | 7/2015 | Inoue | |
| 2016/0338652 | A1 | 11/2016 | Yoshioka et al. | |

* cited by examiner

| NURSED PERSON | UNMONITORED PERIOD (sec) | UNMEASURABLE PERIOD (sec) |
|---|---|---|
| 1 | 65 | 0 |
| 2 | 105 | 2 |
| 3 | 5 | 0 |
| 4 | 145 | 10 |
| 5 | 225 | 0 |
| 6 | 205 | 0 |
| 7 | 125 | 18 |
| 8 | 165 | 12 |
| 9 | 185 | 0 |
| 10 | 85 | 0 |
| 11 | 45 | 3 |
| 12 | 25 | 0 |

| NURSED PERSON | UNMONITORED PERIOD (sec) | UNMEASURABLE PERIOD (sec) |
|---|---|---|
| 1 | 65 | 0 |
| 2 | 105 | 2 |
| 3 | 5 | 0 |
| 4 | 145 | 10 |
| 5 | 225 | 0 |
| 6 | 205 | 0 |
| 7 | 125 | 18 |
| 8 | 165 | 12 |
| 9 | 185 | 0 |
| 10 | 85 | 0 |
| 11 | 45 | 3 |
| 12 | 25 | 0 |

MONITORING SUPPORT APPARATUS AND MONITORING SUPPORT METHOD FOR SUPPORTING WORK OF MONITORING PERSON WHO MONITORS PLURALITY OF SUBJECTS BY SEQUENTIALLY VISITING THE PLURALITY OF SUBJECTS

CROSS REFERENCE TO RELATED APPLICATIONS

This is a continuation of U.S. patent application Ser. No. 17/000,431, filed Aug. 24, 2020, which is a continuation of International Patent Application No. PCT/JP2019/018317, filed May 8, 2019, which claims priority to Japanese Patent Application No. 2018-104066, filed May 30, 2018, and to Japanese Patent Application No. 2019-061402, filed Mar. 27, 2019. The entire disclosure of each of the above-identified documents, including the specification, drawings, and claims, is incorporated herein by reference in its entirety.

BACKGROUND

1. Technical Field

The present disclosure relates to a monitoring support apparatus and a monitoring support method for supporting patrolling and monitoring work of a monitoring person who monitors a plurality of subjects.

2. Description of the Related Art

Conventionally, monitoring devices for monitoring subjects such as infants are known. International Publication No. 2016/151966 discloses, as an example of this kind of monitoring device, a monitoring device that determines whether or not a sleeping infant is exhibiting a sign of sudden infant death syndrome by taking an image of the infant by using a camera and gives an notification to an outside if such a sign is found.

SUMMARY

One non-limiting and exemplary embodiment provides a monitoring support apparatus and a monitoring support method that lessen a burden of patrolling and monitoring operation of a monitoring person who monitors subjects.

In one general aspect, the techniques disclosed here feature a monitoring support apparatus for supporting work of a monitoring person who monitors a plurality of subjects by sequentially visiting the plurality of subjects, including: a measuring device that measures the plurality of subjects and the monitoring person by radiating a detecting wave toward the plurality of subjects and the monitoring person; a position specifying circuit that specifies positions of the plurality of subjects and a position of the monitoring person on a basis of information obtained by the measuring device; and a decision circuit that decides at least one selected from a group consisting of a next subject suitable as a subject to be visited next by the monitoring person among the plurality of subjects and a movement path along which the monitoring person moves from the position of the monitoring person to the next subject on a basis of the positions of the plurality of subjects and the position of the monitoring person specified by the position specifying circuit.

A burden on a monitoring person who patrols and monitors subjects can be lessened.

It should be noted that general or specific embodiments of the present disclosure may be implemented as a system, a method, an integrated circuit, a computer program, a computer-readable storage medium such as a CD-ROM, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 illustrates a storage table stored in the memory of the monitoring support apparatus according to the exemplary embodiment;

FIG. 13 illustrates a storage table stored in the memory of the monitoring support apparatus illustrated in FIG. 12;

DETAILED DESCRIPTION

Figure 1:
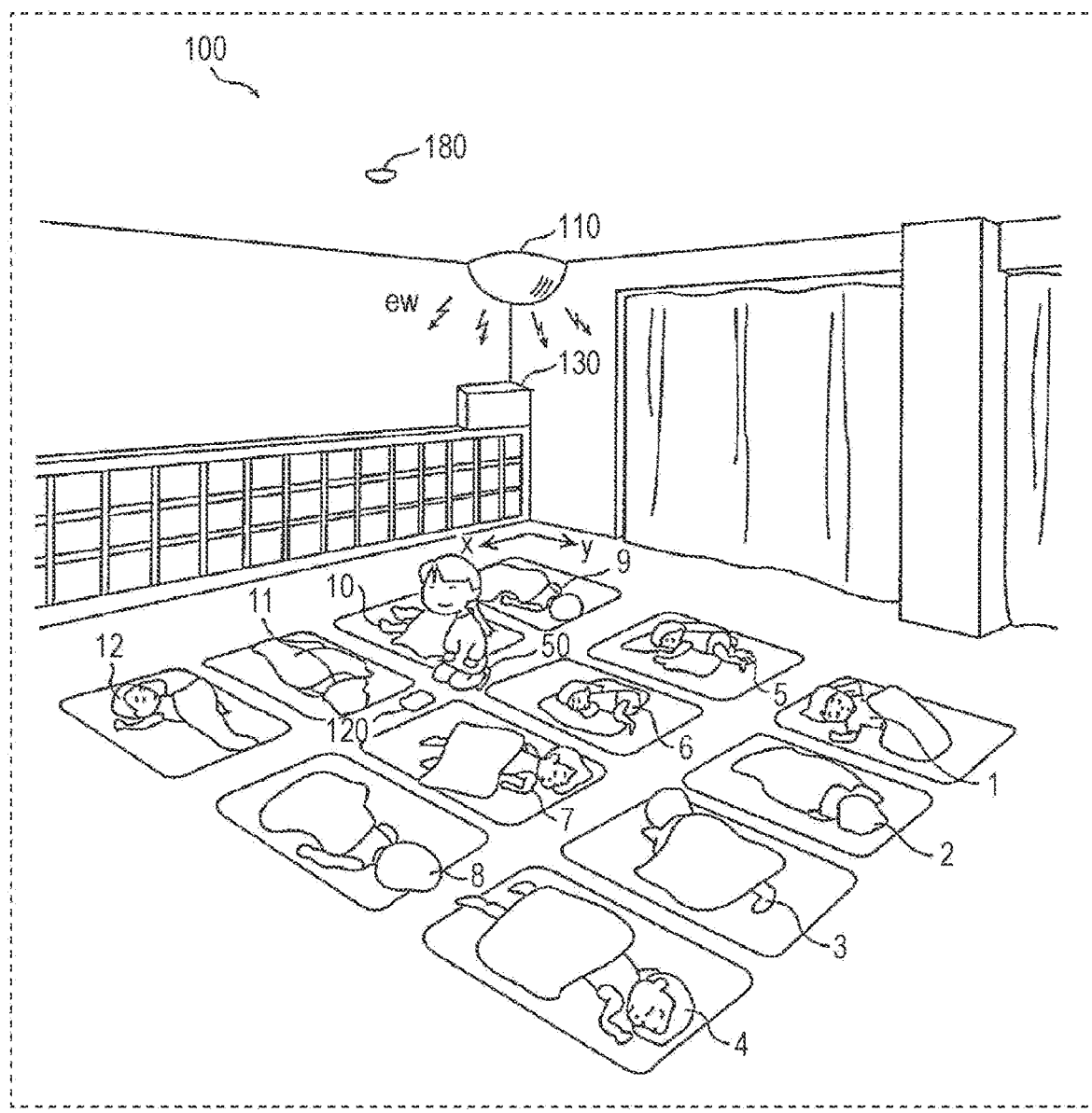
FIG. 1 schematically illustrates a monitoring support apparatus according to an exemplary embodiment.

Underlying Knowledge Forming Basis of the Present Disclosure

For example, in a case where nursed persons such as infants who are taking an afternoon nap are monitored as subjects, a nursing personnel such as a nursery school teacher is required to regularly patrol as a monitoring person to check the nursed persons instead of monitoring the nursed persons by using a monitoring device only. A conventional monitoring device that monitors nursed persons by using a non-contact sensor such as a camera undesirably cannot detect a nursed person hidden behind a nursing personnel when viewed from the non-contact sensor, that is, a nursed person in a blind spot since the nursing personnel blocks a detection range of the non-contact sensor. If such a state where the monitoring device cannot detect a nursed person continues for a long time, the monitoring device notifies the nursing personnel about occurrence of an abnormal state even though the nursed person is in a normal state. This undesirably imposes a burden on the patrolling work of the nursing personnel.

As a result of studies on the above problems, the inventor accomplished a monitoring support apparatus and a monitoring support method that lessen a burden on patrolling and monitoring work of a monitoring person.

A monitoring support apparatus according to an aspect of the present disclosure is for supporting work of a monitoring person who monitors a plurality of subjects by sequentially visiting the plurality of subjects and includes a measuring device that measures the plurality of subjects and the monitoring person by radiating a detecting wave toward the plurality of subjects and the monitoring person; a position specifying circuit that specifies positions of the plurality of subjects and a position of the monitoring person on a basis of information obtained by the measuring device; and a decision circuit that decides at least one selected from a group consisting of a next subject suitable as a subject to be visited next by the monitoring person among the plurality of subjects and a movement path along which the monitoring person moves from the position of the monitoring person to the next subject on a basis of the positions of the plurality of subjects and the position of the monitoring person specified by the position specifying circuit.

According to this configuration, it is possible to save the monitoring person the trouble of deciding a subject who should be visited next or the trouble of deciding a movement path to the subject who should be visited next. This can lessen a burden of patrolling and monitoring work of the monitoring person.

The monitoring support apparatus may be configured to further include an input unit by which the monitoring person enters monitoring information on monitoring results and monitoring times of monitoring of the plurality of subjects, wherein the decision circuit decides the at least one selected from the group consisting of the next subject and the movement path on a basis of the monitoring information.

According to this configuration, at least one of the subject who should be visited next and the movement path can be decided by referring to monitoring information of the subjects. This can lessen a burden of the patrolling and monitoring work of the monitoring person.

The monitoring support apparatus may be configured such that the decision circuit acquires, for each of the plurality of subjects, an unmonitored period for which the subject is not being monitored by the monitoring person by using the monitoring information and decides the at least one selected from the group consisting of the next subject and the movement path so that the unmonitored period of each of the plurality of subjects falls within a predetermined unmonitored period.

According to this configuration, the monitoring person can do the patrolling and monitoring work without anxiety since there is no concern that the unmonitored period will exceed the predetermined unmonitored period.

The monitoring support apparatus may be configured such that the decision circuit acquires, for each of the plurality of subjects, an unmeasurable period in which the subject is unmeasurable by the measuring device because of the each of the plurality of subjects being hidden behind the monitoring person by using the information and decides the at least one selected from the group consisting of the next subject and the movement path so that the unmeasurable period of each of the plurality of subjects falls within a predetermined unmeasurable period.

According to this configuration, the monitoring person can do the patrolling and monitoring work without anxiety since there is no concern that the unmeasurable period exceeds the predetermined unmeasurable period.

The monitoring support apparatus may be configured such that the measuring device further measures biological information of the plurality of subjects; and the decision circuit decides the at least one selected from the group consisting of the next subject and the movement path on a basis of the biological information.

According to this configuration, at least one of the subject who should be visited next and the movement path can be decided by referring to biological information of the subjects. This allows the monitoring person to do the patrolling and monitoring work without anxiety.

The monitoring support apparatus may be configured such that the decision circuit acquires, for each of the plurality of subjects, an unmonitored period for which the subject is not being monitored by the monitoring person by using the monitoring information and decides, as the next subject, a subject who has a longest unmonitored period among the plurality of subjects.

According to this configuration, at least one of the subject who should be visited next and the movement path can be decided by referring to a subject who has a longest unmonitored period. This allows the monitoring person to do the patrolling and monitoring work without anxiety.

The monitoring support apparatus may be configured such that the decision circuit decides the movement path so that a distance over which the monitoring person moves to the next subject becomes shortest.

According to this configuration, a burden of the patrolling and monitoring work of the monitoring person can be lessened since a distance over which the monitoring person moves is shortened.

The monitoring support apparatus may be configured such that the detecting wave is an electromagnetic wave.

According to this configuration, a burden of the patrolling and monitoring work of the monitoring person can be lessened since a distance, a direction, and an elevation angle from a target and movement of the target can be measured in a non-contact manner.

The monitoring support apparatus may be configured such that the decision circuit decides the movement path so that a situation where a predetermined subject among the plurality of subjects is not irradiated with the electromagnetic wave does not occur in a case where the monitoring person moves to the next subject.

According to this configuration, an unmeasurable period of a predetermined subject can be shortened. This can lessen work of checking an unmeasurable period done by the monitoring person, thereby lessening a burden of the patrolling and monitoring work of the monitoring person.

The monitoring support apparatus may be configured such that the decision circuit includes an extraction circuit that extracts a subject who is unmeasurable by the measuring device among the plurality of subjects on a basis of a relationship among the positions of the plurality of subjects, the position of the monitoring person, and a position of the measuring device; and the decision circuit decides the movement path so that the subject who is unmeasurable by the measuring device is irradiated with the electromagnetic wave in a case where the monitoring person moves to the next subject.

According to this configuration, an unmeasurable period of a subject which the measuring device failed to measure can be reset to 0 seconds. This can lessen work of checking an unmeasurable period done by the monitoring person, thereby lessening a burden of the patrolling and monitoring work of the monitoring person.

The monitoring support apparatus may be configured to further include a notification device that notifies the monitoring person about the at least one selected from the group consisting of the next subject and the movement path.

According to this configuration, a burden of the patrolling and monitoring work of the monitoring person can be lessened since the monitoring person can be notified about at least one of the subject who should be visited next and the movement path.

The monitoring support apparatus may be configured such that the notification device notifies the monitoring person about the movement path by irradiating the movement path with visible light.

According to this configuration, a burden of the patrolling and monitoring work of the monitoring person can be lessened since the monitoring person can be moved along the movement path indicated by visible light.

A monitoring support method according to an aspect of the present disclosure is for supporting work of a monitoring person who monitors a plurality of subjects by sequentially visiting the plurality of subjects and includes measuring the plurality of subjects and the monitoring person by radiating a detecting wave toward the plurality of subjects and the monitoring person; specifying positions of the plurality of subjects and a position of the monitoring person on a basis of information obtained by the measuring; and deciding at least one selected from a group consisting of a next subject suitable as a subject to be visited next by the monitoring person among the plurality of subjects and a movement path along which the monitoring person moves from the position of the monitoring person to the next subject on a basis of the positions of the plurality of subjects and the position of the monitoring person.

According to this method, the monitoring person can be saved the trouble of deciding a subject who should be visited next or the trouble of deciding a movement path to the subject who should be visited next. This can lessen the burden of the patrolling and monitoring work of the monitoring person.

The monitoring support method may further include acquiring monitoring information on monitoring results and monitoring times of the plurality of subjects, wherein in the deciding, the at least one selected from the group consisting of the next subject and the movement path is decided on a basis of the monitoring information.

According to this method, at least one of the subject who should be visited next and the movement path can be decided by referring to monitoring information of the subjects. This can lessen the burden of the patrolling and monitoring work of the monitoring person.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or a large scale integration (LSI). The LSI or IC can be integrated into one chip, or also can be a combination of plural chips. For example, functional blocks other than a memory may be integrated into one chip. The name used here is LSI or IC, but it may also be called system LSI, very large scale integration (VLSI), or ultra large scale integration (ULSI) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

A monitoring support apparatus and a monitoring support method according to an aspect of the present disclosure are described in detail below with reference to the drawings.

In the exemplary embodiment described below, it is, for example, assumed that a subject and a monitoring person are a nursed person such as an infant having an afternoon nap and a nursing personnel such as a nursery school teacher, respectively.

The exemplary embodiment described below illustrates a specific example of the present disclosure. Numerical values, shapes, materials, constituent elements, ways in which the constituent elements are disposed and connected, steps, an order of steps, and the like in the exemplary embodiment below are examples and do not limit the present disclosure. Among the constituent elements in the exemplary embodiment below, constituent elements that are not recited in an independent claim showing a highest-order concept are described as optional constituent elements.

EXEMPLARY EMBODIMENT

1. Configuration of Monitoring Support Apparatus

Figure 2:
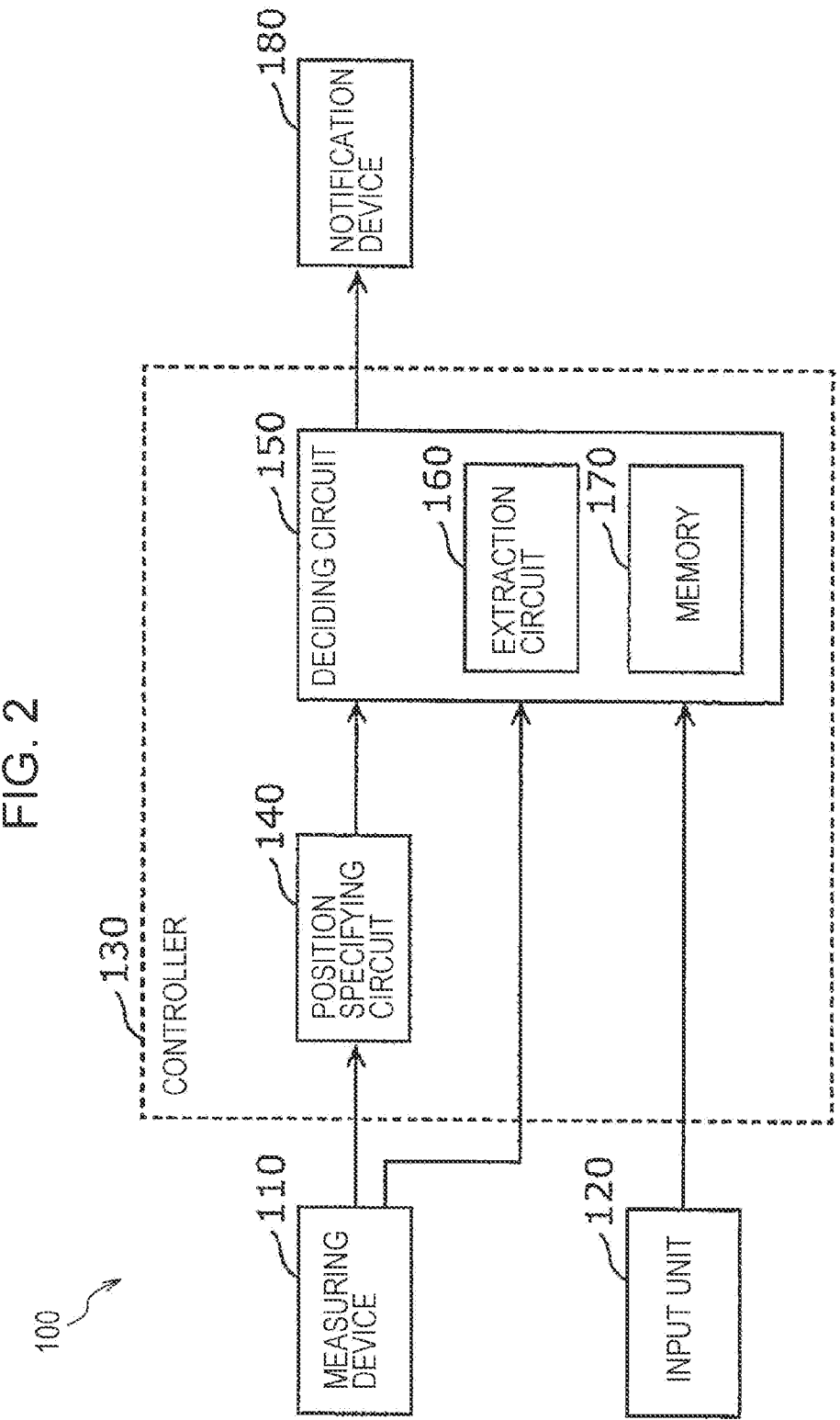
FIG. 2 is a block diagram illustrating a functional configuration of the monitoring support apparatus according to the exemplary embodiment.

FIG. 1 schematically illustrates a monitoring support apparatus 100 according to an exemplary embodiment. FIG. 2 is a block diagram illustrating a functional configuration of the monitoring support apparatus 100.

FIG. 1 illustrates the monitoring support apparatus 100 that supports monitoring of nursed persons 1 to 12 in a building. The monitoring support apparatus 100 detects whether the nursed persons 1 to 12 are in a normal condition or an abnormal condition by measuring breathing, heartbeats, and/or the like of the nursed persons 1 to 12. Note that the number of nursed persons is not limited to 12, provided that the number of nursed persons is 3 or more.

FIG. 1 also illustrates a nursing personnel 50 who moves in the building. The nursing personnel 50 checks the nursed persons 1 to 12 who are taking an afternoon nap to make sure that the nursed persons 1 to 12 are not in an abnormal condition by patrolling and monitoring the nursed persons 1 to 12.

As illustrated in FIGS. 1 and 2, the monitoring support apparatus 100 includes a measuring device 110, an input unit 120, a controller 130 having a position specifying circuit 140 and a decision circuit 150, and a notification device 180. As illustrated in FIG. 1, the measuring device 110 and the notification device 180 are on a ceiling of the building, and the controller 130 is disposed at a corner of the building. The input unit 120 is carried by the nursing personnel 50.

The measuring device 110 is a device that measures the nursed persons 1 to 12 or the nursing personnel 50 in the building by radiating an electromagnetic wave as an example of a detecting wave. Specifically, the measuring device 110 measures a distance, a direction, an elevation angle, and the like of each of the nursed persons 1 to 12 or the nursing personnel 50 from the measuring device 110. Furthermore, the measuring device 110 measures movement (e.g., breathing or heartbeats) of the nursed persons 1 to 12 by radiating an electromagnetic wave to detect biological information of the nursed persons 1 to 12. The biological information is detected by a known radar signal processing method (see, for example, Japanese Unexamined Patent Application Publication No. 2016-214876).

The measuring device 110 is, for example, a Doppler radar. The measuring device 110 emits an electromagnetic wave, which is a detecting wave, in the building and receives a wave reflected by a target to be measured. In this way, the measuring device 110 measures a distance, a direction, an elevation angle to the target to be measured and movement of the target to be measured in a non-contact manner. The target to be measured is detected by a known radar signal processing method (see, for example, Japanese Patent No. 4977806). The electromagnetic wave has, for example, a frequency in a millimeter waveband of not less than 30 GHz to not more than 300 GHz. The measuring device 110 may measure the target to be measured in a non-directional mode in which none of transmission directivity of the detecting wave and reception directivity of the reflected wave are controlled or may measure the target to be measured in a directional mode in which at least one of the transmission directivity and the reception directivity is controlled. Measurement information obtained by the measuring device 110 is supplied to the controller 130.

In a case where the measuring device 110 is configured as above, the nursing personnel 50 who is patrolling is sometimes located between the measuring device 110 and any of the nursed persons 1 to 12. This creates a state (occlusion) in which the measuring device 110 cannot measure a nursed person who is hidden behind the nursing personnel 50 when viewed from the measuring device 110.

Figure 3:
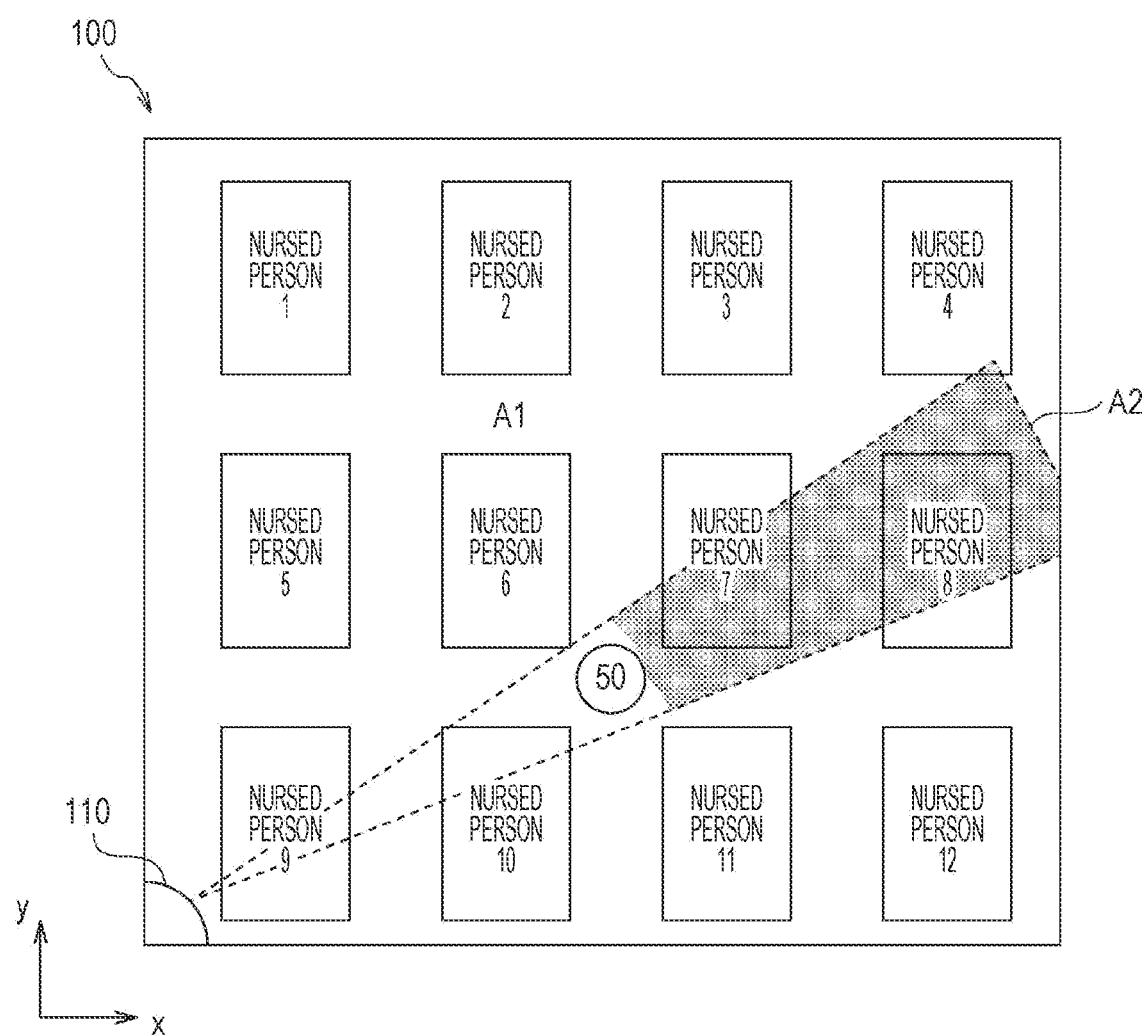
FIG. 3 is a schematic view of a measuring device of the monitoring support apparatus according to the exemplary embodiment, a nursing personnel, and nursed persons viewed from above.

FIG. 3 is a schematic view obtained when the measuring device 110 of the monitoring support apparatus 100, the nursing personnel 50, and the nursed persons 1 to 12 are viewed from above.

FIG. 3 illustrates a measurable region A1 in which a nursed person can be measured by the measuring device 110 and an unmeasurable region (a region indicated by hatching dots) A2 in which a nursed person cannot be measured. Specifically, in FIG. 3, the nursed persons 1 to 3, 5, 6, and 9 to 12 are in the measurable region A1 and the nursed persons 4, 7, and 8 are in the unmeasurable region A2. In FIG. 3, it is assumed that the nursed person 4, who is in a region partially hidden behind the nursing personnel 50, is in the unmeasurable region A2 since measurement information concerning the nursed person 4 cannot be sufficiently obtained.

The monitoring support apparatus 100 according to the present embodiment supports patrolling and monitoring work of the nursing personnel 50 so that a situation where the measuring device 110 cannot measure the nursed persons 1 to 12 becomes less likely to occur. A configuration and a method for supporting the patrolling and monitoring work are described below.

The input unit 120 is a device that receives monitoring information which the nursing personnel 50 enters when monitoring the nursed persons 1 to 12. The input unit 120 is, for example, a mobile terminal such as a smartphone or a tablet terminal. The nursing personnel 50 performs patrolling and monitoring work while carrying the input unit 120 and individually enters monitoring information of the nursed persons 1 to 12.

Figure 4:
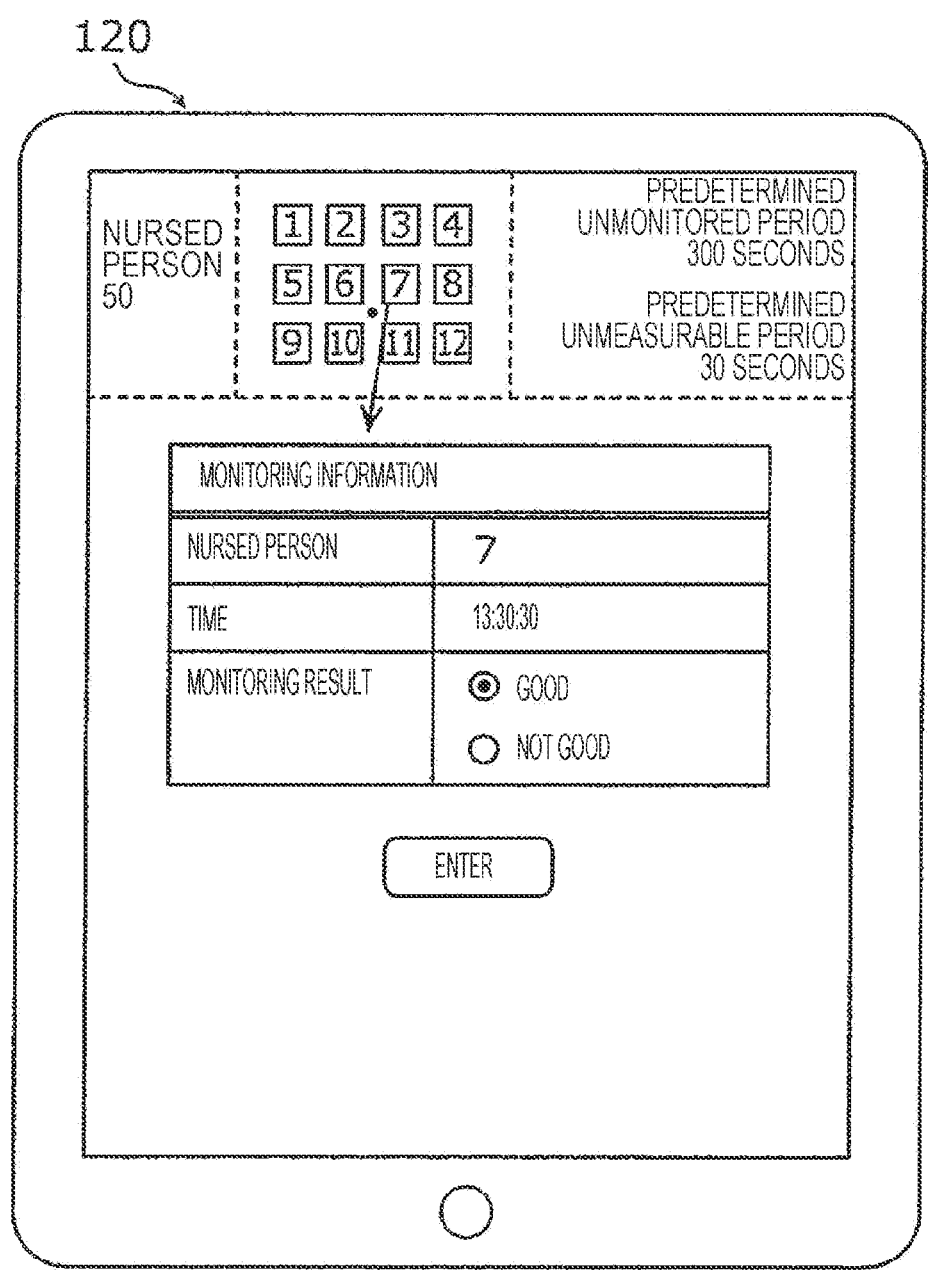
FIG. 4 illustrates an input unit of the monitoring support apparatus according to the exemplary embodiment.

FIG. 4 illustrates the input unit 120 of the monitoring support apparatus 100.

On a screen of the input unit 120 illustrated in FIG. 4, the nursed person 7, who is a monitoring target, a monitoring time at which the nursed person 7 was monitored, and a result of the monitoring are displayed as an example of the monitoring information. The nursing personnel 50 enters the monitoring information by operating the screen of the input unit 120. The monitoring information entered on the input unit 120 is supplied to the controller 130, for example, through wireless communication.

The controller 130 is, for example, a computer that includes a processor, a memory, and a communication circuit. The individual constituent elements of the controller 130 that will be described later may be, for example, software functions realized by execution of programs recorded in the memory by the processor.

As illustrated in FIG. 2, the controller 130 includes the position specifying circuit 140 and the decision circuit 150. The decision circuit 150 includes an extraction circuit 160 and a memory 170. A configuration of the controller 130 is described below in detail.

The position specifying circuit 140 specifies positions of the nursed persons 1 to 12 and a current position of the nursing personnel 50 in the building on the basis of information obtained by the measuring device 110. The position specifying circuit 140 specifies the positions of the nursed persons 1 to 12 and the nursing personnel 50 in the building, for example, by finding the centroid of scattering points of the target to be measured. The positions of the nursed persons 1 to 12 and the current position of the nursing personnel 50 specified by the position specifying circuit 140 are supplied to the extraction circuit 160.

The extraction circuit 160 extracts nursed persons that cannot be measured by the measuring device 110 and nursed persons that can be measured by the measuring device 110 in a distinguishable manner among the nursed persons 1 to 12 on the basis of the positions of the nursed persons 1 to 12 and the current position of the nursing personnel 50 specified by the position specifying circuit 140 and the position of the measuring device 110.

The extraction circuit 160 finds the unmeasurable region A2 that is hidden behind the nursing personnel 50 when viewed from the measuring device 110, for example, while regarding the nursing personnel 50 as a columnar shape approximate model. Then, the extraction circuit 160 extracts the nursed persons who cannot be measured and nursed persons who can be measured by determining whether the nursed persons 1 to 12 are included in the unmeasurable region A2. In the example illustrated in FIG. 3, the nursed persons 4, 7, and 8 are extracted as the nursed persons who cannot be measured by the measuring device 110, and the nursed persons 1 to 3, 5, 6, and 9 to 12 are extracted as the nursed persons who can be measured. Information on whether or not the nursed persons 1 to 12 are measurable extracted by the extraction circuit 160 is supplied to the memory 170. Note that the unmeasurable region A2 may be found by the position specifying circuit 140.

The memory 170 stores therein information obtained by the measuring device 110, information obtained by the extraction circuit 160, and information obtained by the input unit 120. Furthermore, the memory 170 stores therein in advance layout information of the nursed persons 1 to 12, the measuring device 110, and the notification device 180 in the building.

Figure 5:
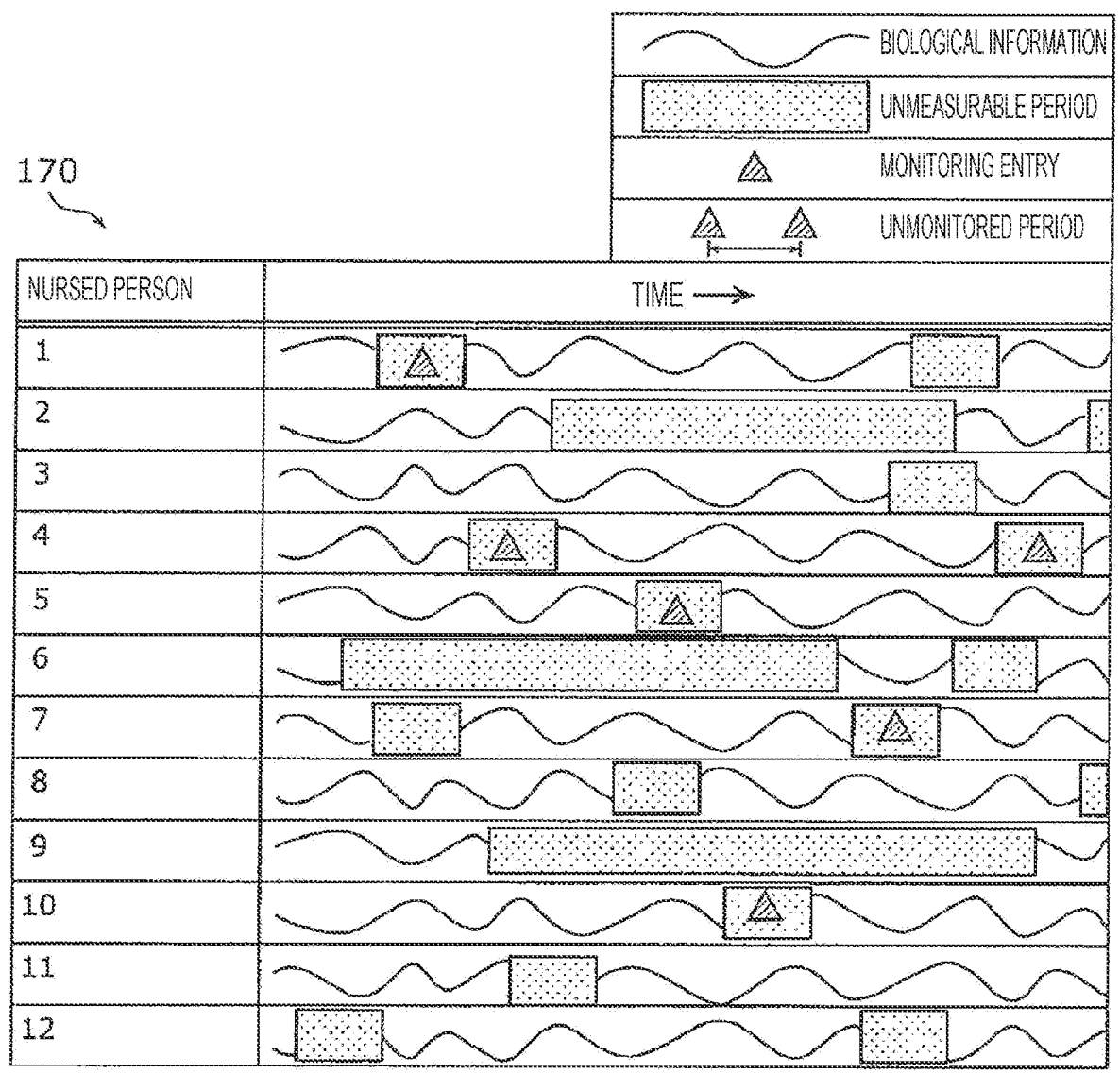
FIG. 5 is a conceptual diagram illustrating measurement information and monitoring information stored in a memory of the monitoring support apparatus according to the exemplary embodiment in chronological order.

FIG. 5 is a conceptual diagram illustrating the measurement information and the monitoring information stored in the memory 170 of the monitoring support apparatus 100 in chronological order.

FIG. 5 illustrates biological information of the nursed persons 1 to 12, which is one of the measurement information. Specifically, breathing states of the nursed persons 1 to 12 are expressed as waves as the biological information.

Furthermore, FIG. 5 illustrates an unmeasurable period, which is one of the measurement information. The unmeasurable period is a period in which a predetermined nursed person is unmeasurable by the measuring device 110 because the predetermined nursed person is hidden behind the nursing personnel 50. The unmeasurable period is accumulated while a state where the nursed person is not irradiated with an electromagnetic wave ew of the measuring device 110 continues and returns to 0 upon irradiation of the electromagnetic wave ew. The monitoring support apparatus 100 supports the patrolling monitoring work so that the unmeasurable period of each of the nursed persons 1 to 12 falls within a predetermined unmeasurable period or so that periods for which the nursed persons 1 to 12 are hidden become short. The predetermined unmeasurable period in the present embodiment is, for example, 30 seconds.

Furthermore, FIG. 5 illustrates monitoring entry, which is one of the monitoring information. The monitoring entry is stored when the nursing personnel 50 ends monitoring of a predetermined nursed person and enters a monitoring result and a monitoring time on the input unit 120.

Furthermore, FIG. 5 illustrates an unmonitored period, which is one of the monitoring information. The unmonitored period refers to a period in which a nursed person is not being monitored by the nursing personnel 50. The unmonitored period is a period from monitoring entry to next monitoring entry and returns to 0 when next monitoring entry is received. The monitoring support apparatus 100 supports the patrolling and monitoring work so that the unmonitored period of each of the nursed persons 1 to 12 falls within a predetermined unmonitored period. The unmonitored period in the present embodiment is, for example, 300 seconds.

FIG. 6 illustrates a storage table stored in the memory 170 of the monitoring support apparatus 100. Note that FIG. 6 illustrates a scene different from FIG. 5.

In the storage table of FIG. 6, unmonitored periods and unmeasurable periods of the nursed persons 1 to 12 are illustrated. In FIG. 6, the unmonitored period of the nursed person 5 is 225 seconds, which is longest among the unmonitored periods of the nursed persons 1 to 12. The unmeasurable periods of the nursed persons 4, 7, and 8 are 10 seconds, 18 seconds, and 12 seconds, respectively, which are longer than the unmeasurable periods of the other nursed persons 1 to 3, 5, 6, and 9 to 12. Note that the unmeasurable periods of the nursed persons 2 and 11 occur because the nursed persons 2 and 11 temporarily become unmeasurable due to movement such as roll-over. These unmeasurable periods return to 0 second relatively early and are not regarded as a problem.

The decision circuit 150 decides a nursed person who should be visited next among the nursed persons 1 to 12 and a movement path R1 that connects the nursing personnel 50 and the nursed person who should be visited next by using these pieces of information stored in the memory 170. Specifically, the decision circuit 150 decides the nursed person who should be visited next and the movement path R1 so that the unmonitored period of each of the nursed persons 1 to 12 falls within the predetermined unmonitored period on the basis of the positions of the nursed persons 1 to 12 and the current position of the nursing personnel 50 specified by the position specifying circuit 140. Furthermore, the decision circuit 150 decides the nursed person who should be visited next and the movement path R1 so that the unmeasurable period of each of the nursed persons 1 to 12 falls within the predetermined unmeasurable period. The decision circuit 150 may decide the nursed person who should be visited next and the movement path R1 by using mathematical programming or artificial intelligence to solve a constraint satisfaction problem that meets both of the condition that the unmonitored periods fall within the predetermined unmonitored period and the condition that the unmeasurable periods fall within the predetermined unmeasurable period.

The decision circuit 150 may decide the nursed person who should be visited next on the basis of not only the various kinds of information described above but also the biological information of the nursed persons 1 to 12 measured by the measuring device 110. For example, in a case where the nursed persons 1 to 12 include a person who is in an unstable state, the decision circuit 150 may decide the nursed person who is in an unstable state as a top-priority person to be visited.

Figure 7:
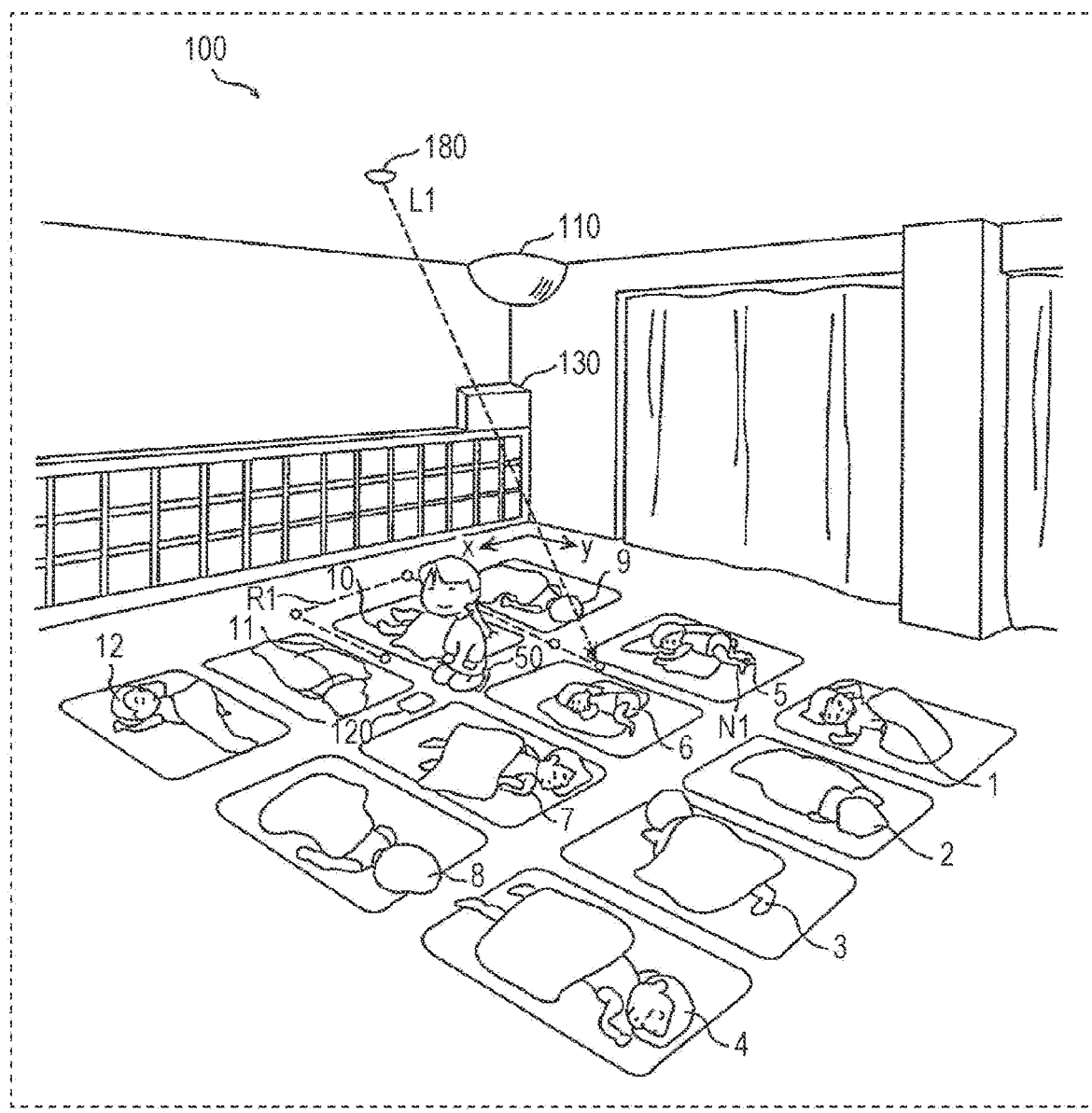
FIG. 7 illustrates an example of operation of a notification device of the monitoring support apparatus according to the exemplary embodiment.

The notification device 180 is a device that notifies the nursing personnel 50 about the nursed person who should be visited next and the movement path R1 decided by the decision circuit 150. FIG. 7 illustrates an example of operation of the notification device 180 of the monitoring support apparatus 100.

The notification device 180 is, for example, a projection mapping device and navigates the nursing personnel 50 along the movement path R1 from the current position of the nursing personnel 50 to the nursed person N1 who should be visited next (e.g., the nursed person 5) by using visible light L1. The nursing personnel 50 moves along the movement path R1. This allows the nursing personnel 50 to efficiently perform the patrolling and monitoring work of the nursed persons 1 to 12. That is, the monitoring support apparatus 100 configured as above can lessen a burden on the nursing personnel 50 who does the work of patrolling and monitoring the nursed persons 1 to 12.

2. Monitoring Support Method

Figure 8:
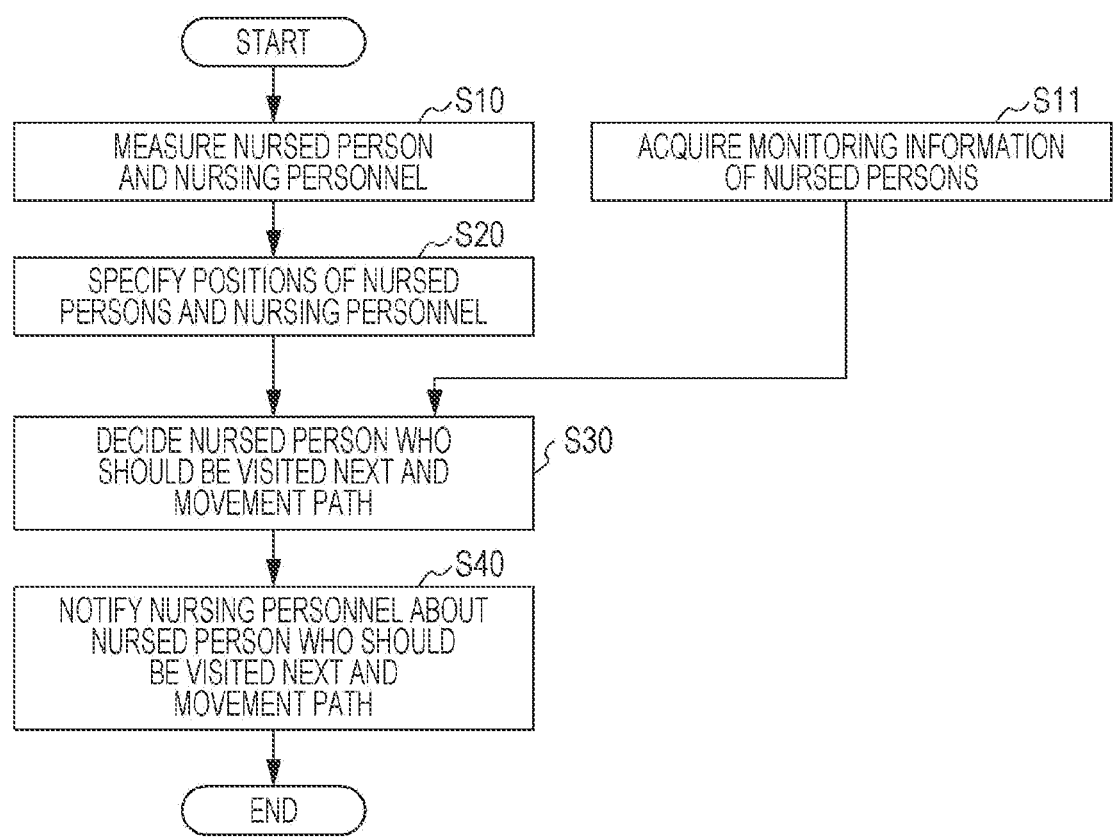
FIG. 8 is a flowchart illustrating a monitoring support method according to the exemplary embodiment.

Next, a monitoring support method using the monitoring support apparatus 100 is described. FIG. 8 is a flowchart illustrating a monitoring support method according to the exemplary embodiment.

First, the measuring device 110 measures the nursed persons 1 to 12 and the nursing personnel 50 by radiating an electromagnetic wave toward the nursed persons 1 to 12 and the nursing personnel 50 (step S10).

Next, the position specifying circuit 140 of the controller 130 specifies positions of the nursed persons 1 to 12 and a current position of the nursing personnel 50 in the building on the basis of the information obtained in step S10 (step S20).

Meanwhile, the nursing personnel 50 does work of patrolling and monitoring the nursed persons 1 to 12 and enters monitoring information on monitoring results and monitoring times of the nursed persons 1 to 12 on the input unit 120. In this way, the input unit 120 acquires the monitoring information (step S11).

Next, the decision circuit 150 of the controller 130 decides a nursed person N1 who should be visited next among the nursed persons 1 to 12 and a movement path R1 that connects the nursing personnel 50 and the nursed person N1 who should be visited next on the basis of the positions of the nursed persons 1 to 12 and the current position of the nursing personnel 50 specified in step S20 and the monitoring information acquired in step S11 (step S30).

In step S30, the decision circuit 150 may decide the nursed person N1 who should be visited next and the movement path R1 on the basis of only information on the positions specified in step S20. The decision circuit 150 may decide at least one of the nursed person N1 who should be visited next and the movement path R1 in step S30.

Next, the notification device 180 notifies the nursing personnel 50 about the nursed person N1 who should be visited next and the movement path R1 decided by the decision circuit 150 (step S40). Thereafter, steps S10 to S40 are repeatedly executed as needed.

Figure 9:
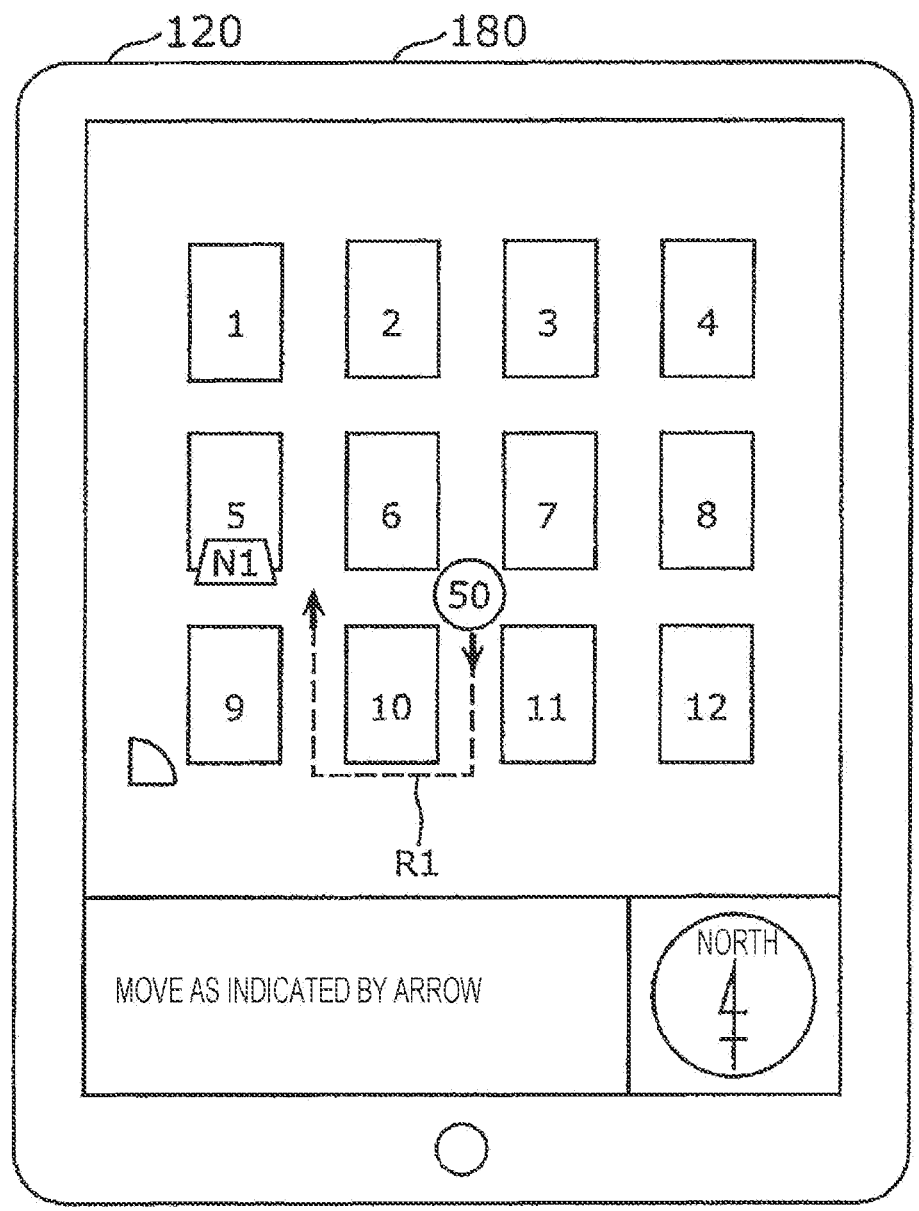
FIG. 9 illustrates another example of the notification device of the monitoring support apparatus according to the exemplary embodiment.

The notification device 180 may notify the nursing personnel 50 about the nursed person N1 who should be visited next and the movement path R1 by using the visible light L1 as illustrated in FIG. 7 or may display the nursed person N1 who should be visited next and the movement path R1 on the screen of the input unit 120 by using the input unit 120 as the notification device 180 as illustrated in FIG. 9.

According to such a monitoring support method, the nursing personnel 50 can save the trouble of thinking who should be visited next and which path he or she should take. This can lessen a burden of the work of patrolling and monitoring the nursed persons 1 to 12.

3. Specific Example of Monitoring Support Apparatus and Monitoring Support Method Next, specific example 1 of the monitoring support apparatus 100 and the monitoring support method is described.

Figure 10:
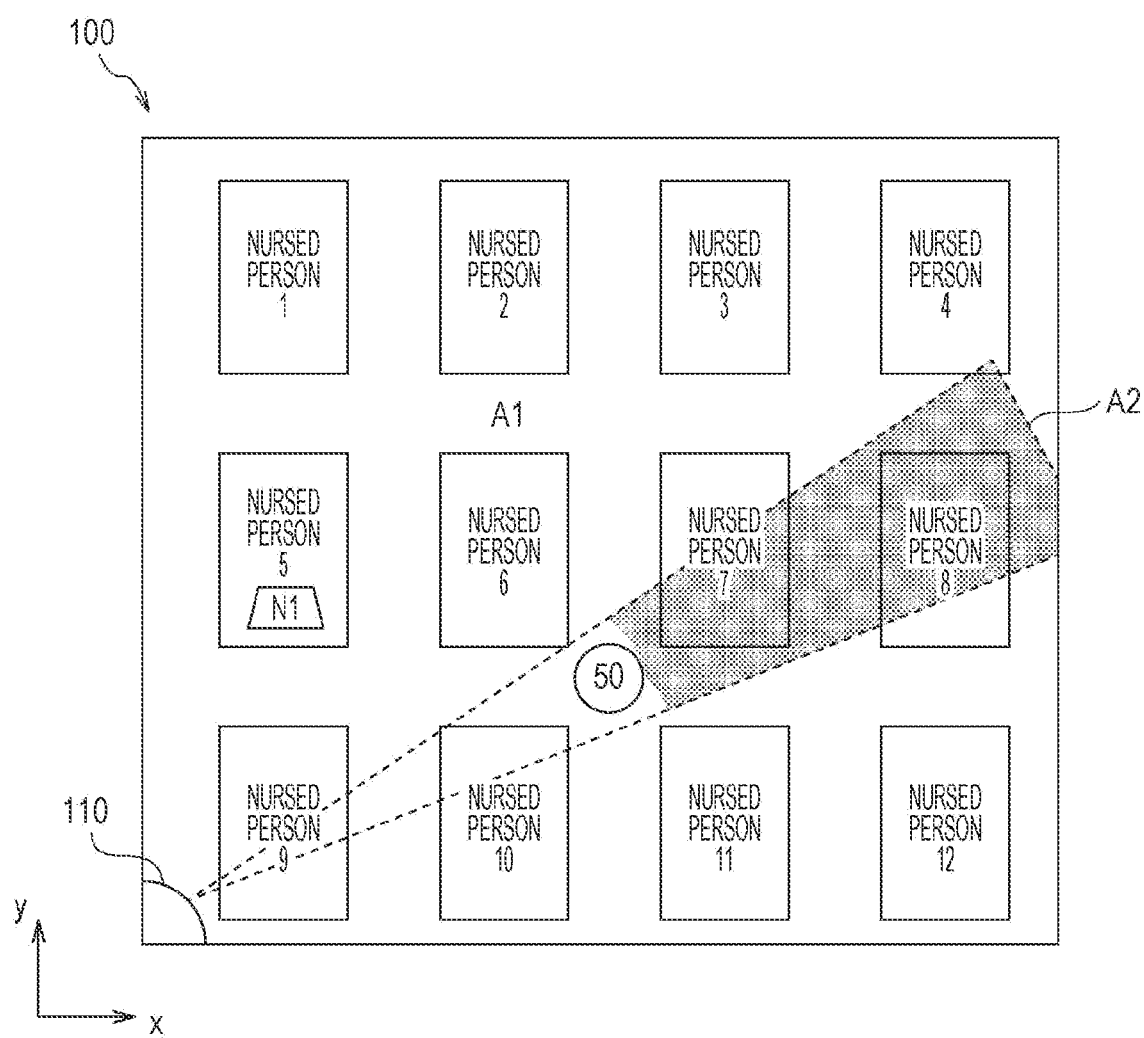
FIG. 10 illustrates a specific example of deciding a nursed person who should be visited next in the monitoring support apparatus according to the exemplary embodiment.
Figure 11:
FIG. 11 illustrates a storage table stored in the memory of the monitoring support apparatus illustrated in FIG. 10.

FIG. 10 illustrates a specific example of deciding the nursed person N1 who should be visited next in the monitoring support apparatus 100. FIG. 11 illustrates a storage table stored in the memory 170 of the monitoring support apparatus 100 illustrated in FIG. 10.

FIG. 10 illustrates a state at a time at which the nursing personnel 50 finishes monitoring the nursed person 7. At this time, the unmonitored period of the nursed person 5 is longest among the unmonitored periods of the nursed persons 1 to 12, as illustrated in FIG. 11. In view of this, the decision circuit 150 of the monitoring support apparatus 100 decides the nursed person 5 as the nursed person N1 who should be visited next among the nursed persons 1 to 12.

Since the decision circuit 150 of the monitoring support apparatus 100 decides a nursed person whose unmonitored period is longest as the nursed person N1 who should be visited next among the nursed persons 1 to 12 as described above, the nursing personnel 50 can save the trouble of deciding the nursed person N1 who should be visited next. This can lessen the burden of the nursing personnel 50.

Next, specific example 2 of the monitoring support apparatus 100 and the monitoring support method is described.

Figure 12:
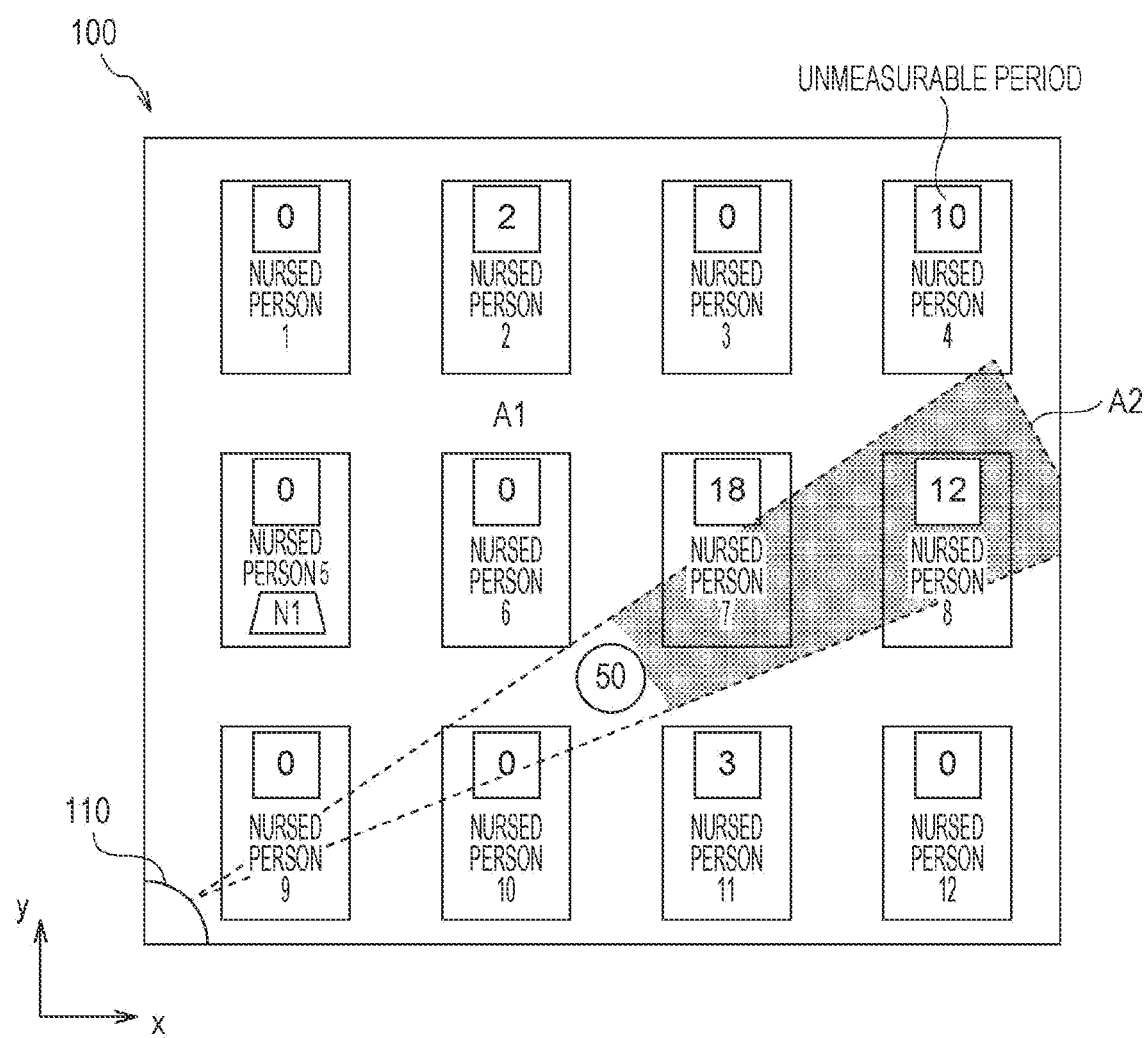
FIG. 12 illustrates a specific example of deciding a movement path of a nursing personnel in the monitoring support apparatus according to the exemplary embodiment.

FIG. 12 illustrates a specific example of deciding the movement path R1 of the nursing personnel 50 in the monitoring support apparatus 100. FIG. 13 illustrates a storage table stored in the memory 170 of the monitoring support apparatus 100 illustrated in FIG. 12.

FIG. 12 illustrates a state at a time at which the nursing personnel 50 finishes monitoring the nursed person 7. At this time, the unmeasurable periods of the nursed persons 4, 7, and 8 are 10 seconds, 18 seconds, and 12 seconds, respectively, which are longer than the unmeasurable periods of the other nursed persons 1 to 3, 5, 6, and 9 to 12, as illustrated in FIG. 13. The unmonitored period of the nursed person 5 is longest among the unmonitored periods of the nursed persons 1 to 12. In view of this, the decision circuit 150 of the monitoring support apparatus 100 decides the movement path R1 so that the nursing personnel 50 arrives at the nursed person N1 who should be visited next as early as possible or so that the unmeasurable period of the nursed person 4, 7, or 8 becomes as short as possible.

Three examples of decision are described below. Note that the nursed person N1 who should be visited next may be decided in advance by the method illustrated in FIGS. 10 and 11 or may be decided based on a command from another external device.

Figure 14A:
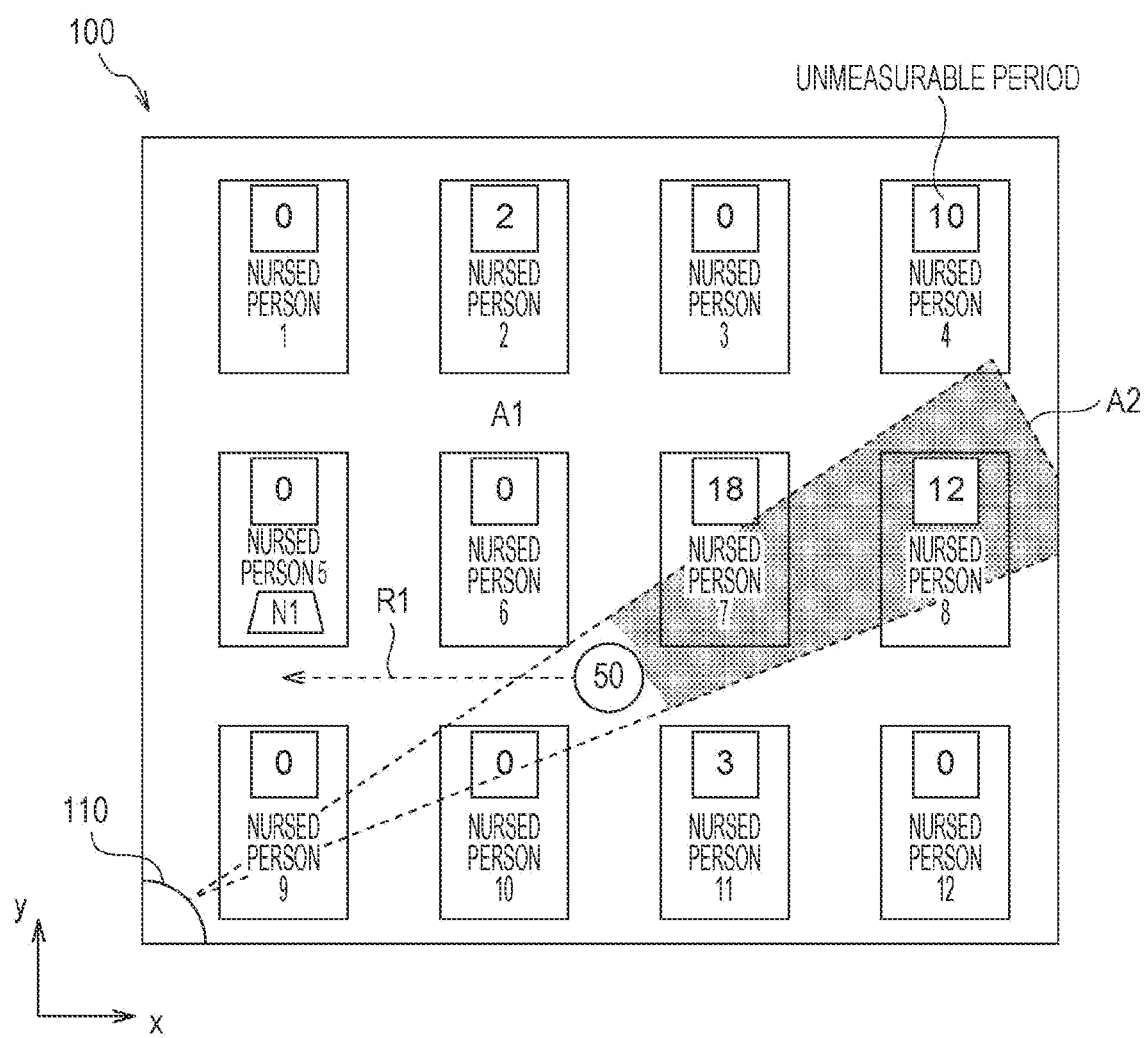
FIG. 14A illustrates an example of a movement path decided by the monitoring support apparatus illustrated in FIG. 12.
Figure 14B:
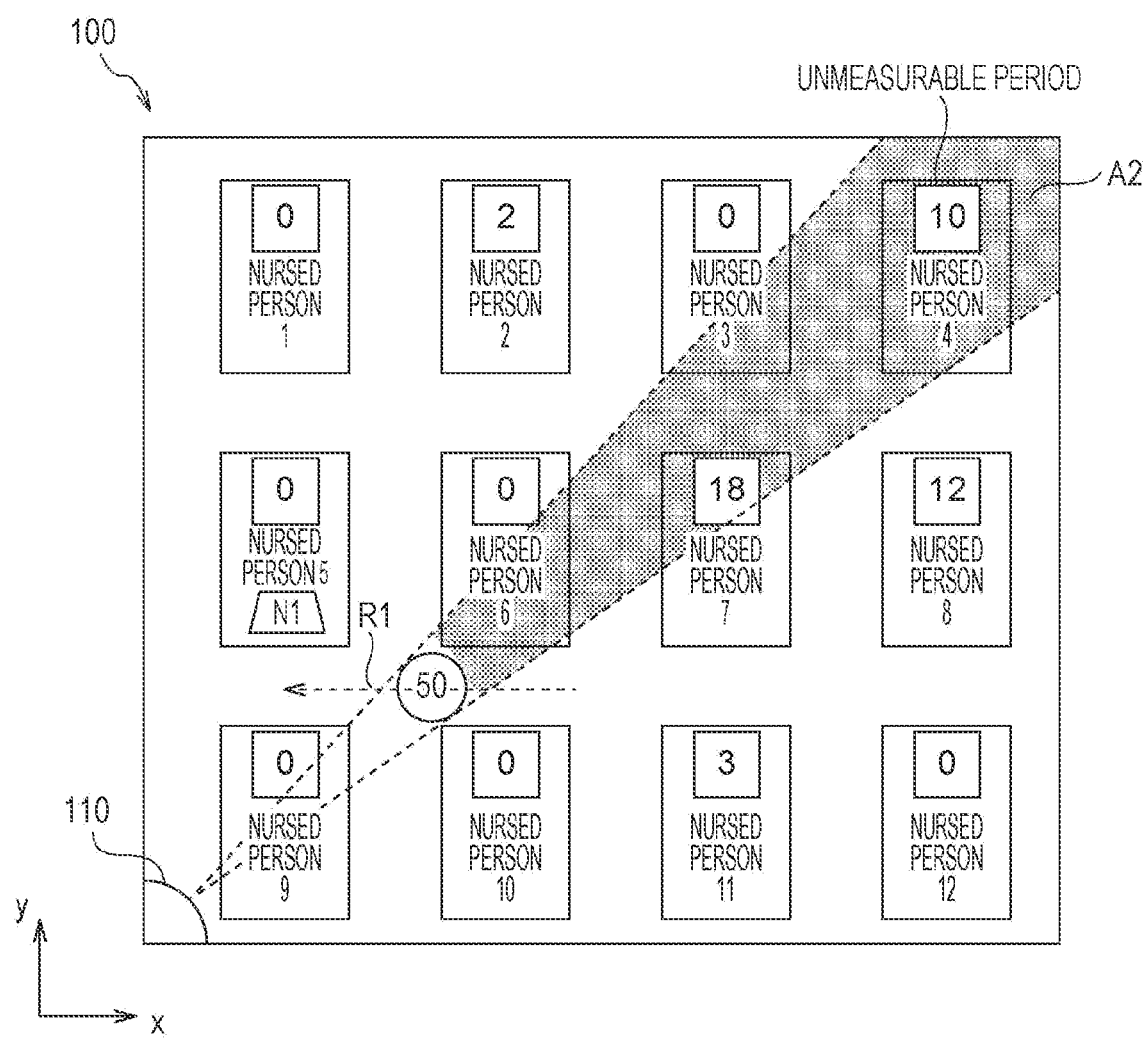
FIG. 14B illustrates an example of a movement path decided by the monitoring support apparatus illustrated in FIG. 12.

First, the first example of decision is described with reference to FIGS. 14A and 14B. FIGS. 14A and 14B illustrate an example of the movement path R1 decided by the monitoring support apparatus 100 illustrated in FIG. 12.

In the first example of decision, the decision circuit 150 decides the movement path R1 so that a distance over which the nursing personnel 50 moves to the nursed person N1 who should be visited next becomes shortest. For example, in a case where the nursed person N1 who should be visited next is the nursed person 5, the decision circuit 150 decides, as the movement path R1, a path connecting the current position of the decision circuit 150 to the nursed person 5 who should be visited next by a straight line. The nursing personnel 50 can arrive at the nursed person 5 in a short time by moving along the movement path R1 from the state illustrated in FIG. 14A, as illustrated in FIG. 14B.

Since the decision circuit 150 decides the movement path R1 so that a distance over which the nursing personnel 50 moves becomes shortest as described above, labor of the nursing personnel 50 can be lessened.

Figure 15A:
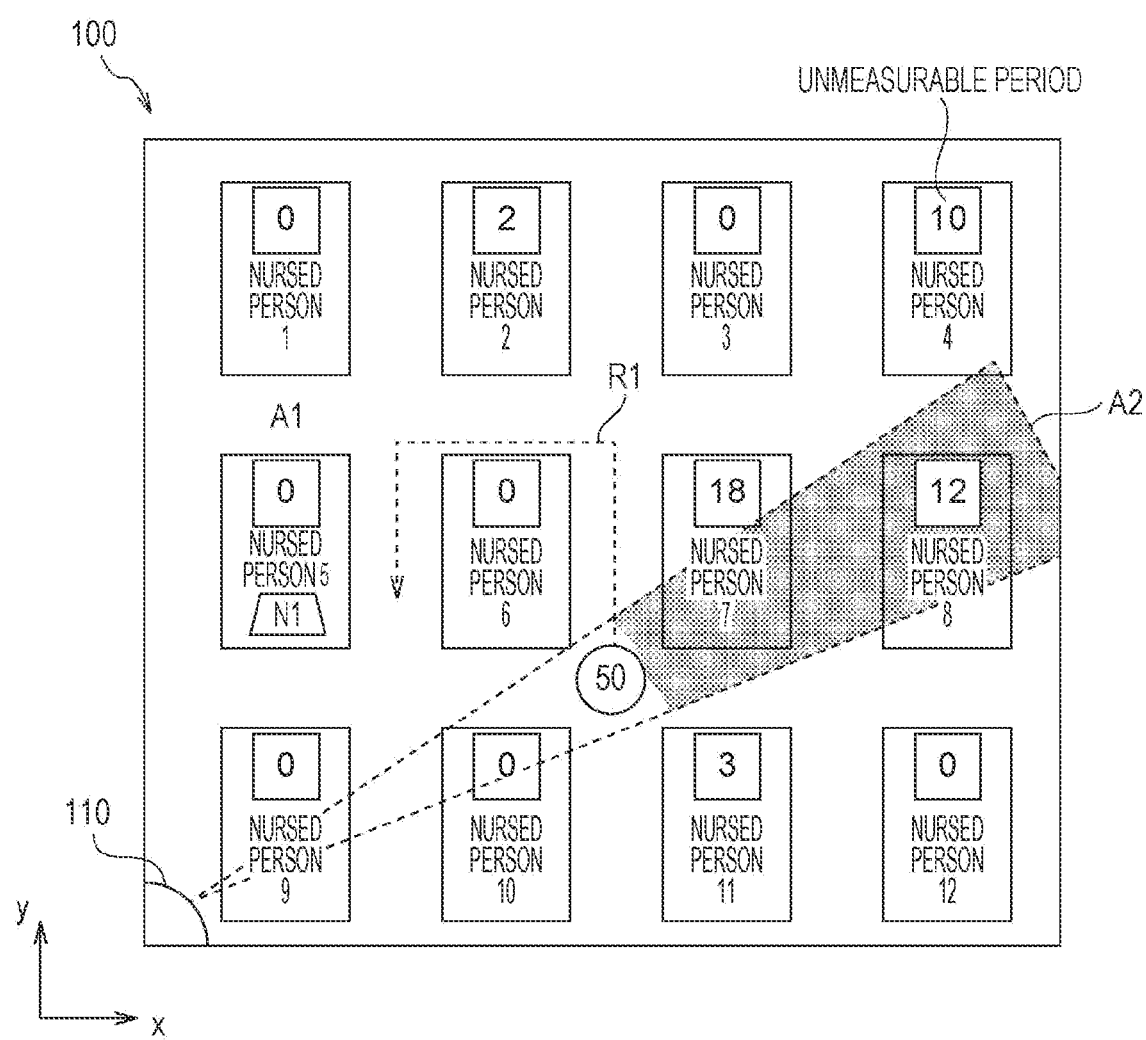
FIG. 15A illustrates another example of a movement path decided by the monitoring support apparatus illustrated in FIG. 12.
Figure 15B:
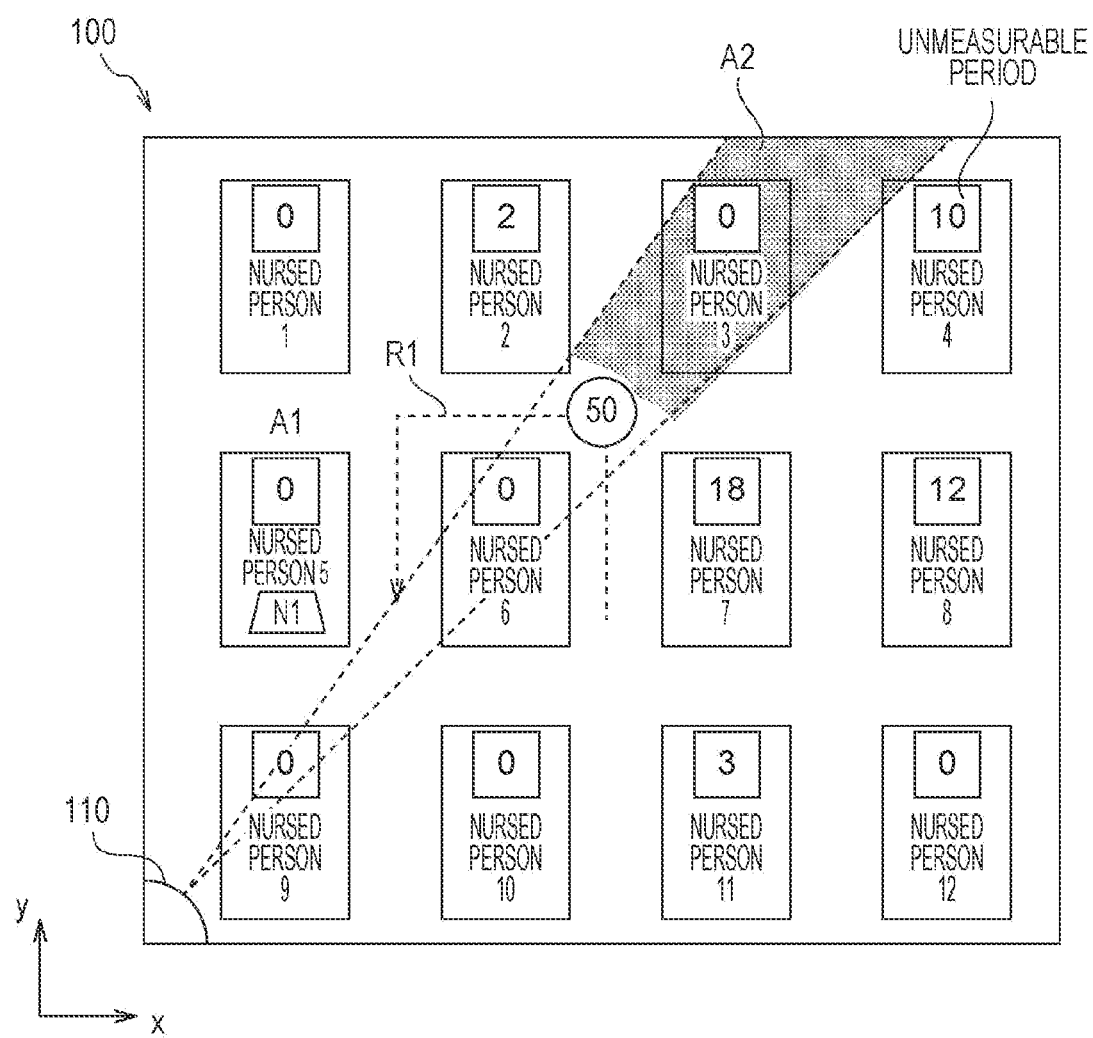
FIG. 15B illustrates another example of a movement path decided by the monitoring support apparatus illustrated in FIG. 12.

Next, the second example of decision is described with reference to FIGS. 15A and 15B. FIGS. 15A and 15B illustrate another example of a movement path decided by the monitoring support apparatus 100 illustrated in FIG. 12.

In the second example of decision, the decision circuit 150 decides the movement path R1 so that a situation where a predetermined nursed person is not irradiated with the electromagnetic wave ew among the nursed persons 1 to 12 does not occur in a case where the nursing personnel 50 moves to the nursed person 5 who should be visited next. For example, the decision circuit 150 decides the movement path R1 so that a situation where the nursed person 6 located between the nursed person 7 whom the nursing personnel 50 has just monitored and the nursed person 5 who should be visited next is not irradiated with the electromagnetic wave ew does not occur, specifically, so that the nursing personnel 50 moves around the nursed person 6 on a far side when viewed from the measuring device 110. In a case where the nursing personnel 50 moves along the movement path R1 from the state illustrated in FIG. 15A as illustrated in FIG. 15B, the unmeasurable period of the nursed person 6 can be shortened.

Since the decision circuit 150 decides the movement path R1 so that a situation where a predetermined nursed person is not irradiated with the electromagnetic wave ew does not occur, the unmeasurable period of the predetermined nursed person can be shortened. This can lessen work of checking the unmeasurable period done by the nursing personnel 50, thereby lessening a burden of the patrolling and monitoring work of the nursing personnel 50.

Figure 16A:
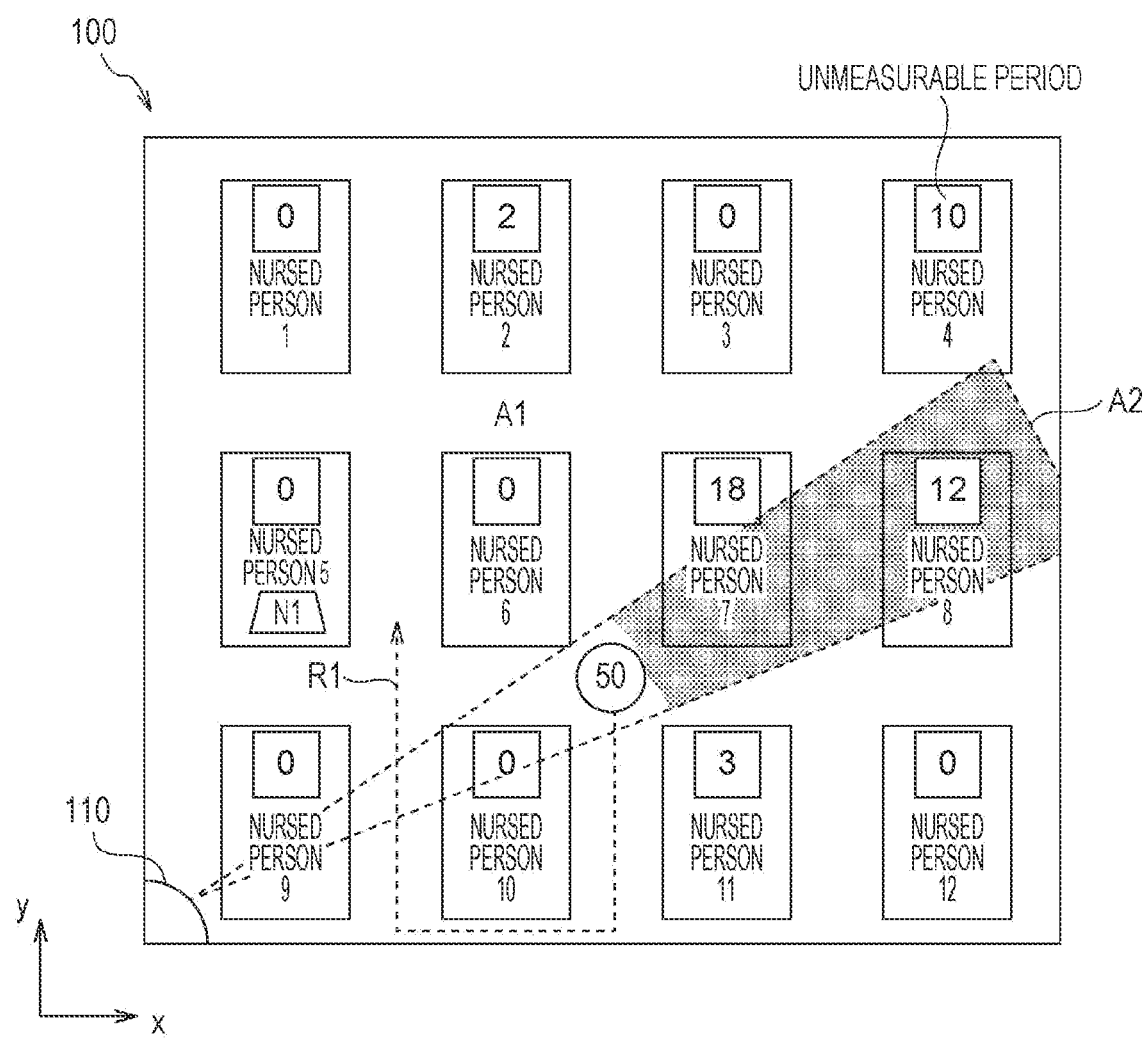
FIG. 16A illustrates still another example of a movement path decided by the monitoring support apparatus illustrated in FIG. 12.
Figure 16B:
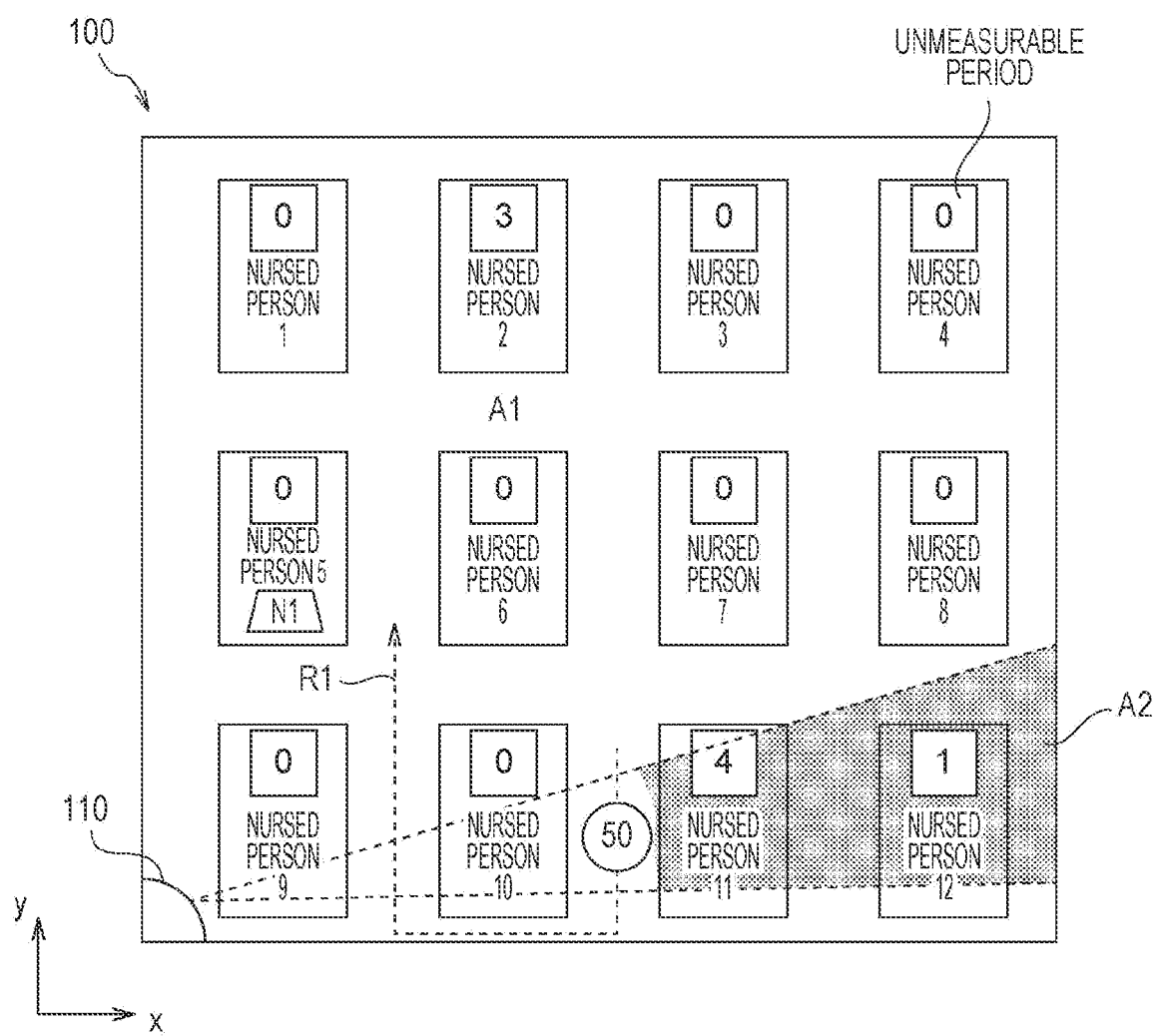
FIG. 16B illustrates still another example of a movement path decided by the monitoring support apparatus illustrated in FIG. 12.

Next, the third example of decision is described with reference to FIGS. 16A and 16B. FIGS. 16A and 16B illustrate still another example of a movement path decided by the monitoring support apparatus 100 illustrated in FIG. 12.

In the third example of decision, the decision circuit 150 decides the movement path R1 so that nursed persons included in the unmeasurable region A2 are irradiated with the electromagnetic wave ew in a case where the nursing personnel 50 moves to the nursed person 5 who should be visited next. For example, the decision circuit 150 decides the movement path R1 so that the nursed persons 4, 7, and 8 who have unmeasurable periods by being blocked by the nursing personnel 50 are irradiated again with the electromagnetic wave ew, that is, so that the nursing personnel 50 is temporarily moved away from a region between the measuring device 110 and the nursed persons 4, 7, and 8. In a case where the nursing personnel 50 moves along this movement path R1 from the state illustrated in FIG. 16A as illustrated in FIG. 16B, unmeasurable periods of the nursed persons 4, 7, and 8 can be returned to 0 second.

Since the decision circuit 150 decides the movement path R1 so that nursed persons who have unmeasurable periods are irradiated with the electromagnetic wave ew as described above, the unmeasurable periods of these nursed persons can be reset to 0 seconds. This can lessen work of checking the unmeasurable periods done by the nursing personnel 50, thereby lessening a burden of the patrolling and monitoring work of the nursing personnel 50.

Other Aspects

Although the monitoring support apparatus and the monitoring support method according to the exemplary embodiment of the present disclosure have been described above, the present disclosure is not limited to the exemplary embodiment. Various modifications of the present embodiment which a person skilled in the art can think of and combinations of constituent elements in different exemplary embodiments may be encompassed within one or more aspects of the present disclosure without departing from the spirit of the present disclosure.

For example, although FIG. 1 of the exemplary embodiment illustrates an example in which the controller 130 is disposed at a corner of the building, this configuration is not restrictive. For example, the controller 130 may be included in the measuring device 110, the notification device 180, or the input unit 120 in an integrated manner. Furthermore, the notification device 180 may be included in the measuring device 110 in an integrated manner.

Furthermore, the decision circuit 150 may cause information calling for attention to be displayed on the screen of the input unit 120 in a case where an unmeasurable period of any of the nursed persons 1 to 12 exceeds a predetermined threshold value. Furthermore, the unmonitored periods and unmeasurable periods of the nursed persons 1 to 12 at a corresponding time may be displayed on the screen of the input unit 120.

Although a nursed person such as an infant having an afternoon nap and a nursing personnel such as a nursery school teacher are used as examples of a subject and a monitoring person, respectively, in the exemplary embodiment of the present disclosure, this is not restrictive. For example, the subject and the monitoring person may be a customer seated at a restaurant and a staff member who take order from customers, respectively, and a movement path along which the staff member takes order from the customers may be decided.

Although an electromagnetic wave is used as an example of a detecting wave that is radiated toward the subject and the monitoring person in the exemplary embodiment of the present disclosure, this is not restrictive. For example, an ultrasonic wave may be applied in consideration of the kind of medium through which the detecting wave propagates, a frequency or a wavelength of the detecting wave, and other conditions. The detecting wave is not limited in particular, provided that a distance, a direction, and an elevation angle from a target to be measured and movement of the target to be measured can be measured in a non-contact manner based on a wave emitted toward the target to be measured and then reflected by the target to be measured under a target environment.

The monitoring support apparatus and the monitoring support method according to the present disclosure are widely applicable to devices and the like that monitor biological information such as a monitoring system in a nursery school, a nursing-care facility, a hospital, or the like or a service system in a restaurant or the like.

What is claimed is:

1. An apparatus comprising:
    a measuring device that measures a plurality of subjects by radiating a detecting wave toward the plurality of subjects;
    a position specifying circuit that specifies positions of the plurality of subjects on a basis of information obtained by the measuring device; and
    a determining circuit that determines
        a next subject suitable as a subject to be visited next by a monitoring person among the plurality of subjects, and/or
        a movement path along which the monitoring person moves from a position of the monitoring person to the next subject on a basis of the positions of the plurality of subjects specified by the position specifying circuit.

2. The apparatus according to claim 1, further comprising an input unit by which the monitoring person enters monitoring information on monitoring results and monitoring times of monitoring of the plurality of subjects,
    wherein the determining circuit determines
        the next subject, and/or
        the movement path,
    on a basis of the monitoring information.

3. The apparatus according to claim 2, wherein
    the determining circuit
        acquires, for each of the plurality of subjects, an unmonitored period for which the subject is not being monitored by the monitoring person by using the monitoring information, and determines the next subject, and/or the movement path, so that the unmonitored period of each of the plurality of subjects falls within a predetermined unmonitored period.

4. The apparatus according to claim 1, wherein the determining circuit acquires, for each of the plurality of subjects, an unmeasurable period in which the subject is unmeasurable by the measuring device, and determines the next subject, and/or the movement path, so that the unmeasurable period of each of the plurality of subjects falls within a predetermined unmeasurable period.

5. The apparatus according to claim 1, wherein the measuring device further measures biological information of the plurality of subjects; and the determining circuit determines the next subject, and/or the movement path, on a basis of the biological information.

6. The apparatus according to claim 2, wherein the determining circuit acquires, for each of the plurality of subjects, an unmonitored period for which the subject is not being monitored by the monitoring person by using the monitoring information, and determines, as the next subject, a subject who has a longest unmonitored period among the plurality of subjects.

7. The apparatus according to claim 1, wherein the determining circuit determines the movement path so that a distance over which the monitoring person moves to the next subject becomes shortest.

8. The apparatus according to claim 1, wherein the detecting wave is an electromagnetic wave.

9. The apparatus according to claim 8, wherein the determining circuit determines the movement path so that a situation where a subject among the plurality of subjects is not irradiated with the electromagnetic wave does not occur in a case where the monitoring person moves to the next subject.

10. The apparatus according to claim 8, wherein the determining circuit includes an extraction circuit that extracts a subject who is unmeasurable by the measuring device among the plurality of subjects on a basis of a relationship among the positions of the plurality of subjects, the position of the monitoring person, and a position of the measuring device; and in a case where the monitoring person moves to the next subject, the determining circuit determines the movement path so that the subject who is unmeasurable by the measuring device is irradiated with the electromagnetic wave.

11. The apparatus according to claim 1, further comprising a notification device that notifies the monitoring person about the next subject, and/or the movement path.

12. The apparatus according to claim 11, wherein the notification device notifies the monitoring person about the movement path by irradiating the movement path with visible light.

13. A method comprising:

measuring a plurality of subjects by radiating a detecting wave toward the plurality of subjects;

specifying positions of the plurality of subjects on a basis of information obtained by the measuring; and determining a next subject suitable as a subject to be visited next by a monitoring person among the plurality of subjects, and/or a movement path along which the monitoring person moves from a position of the monitoring person to the next subject on a basis of the positions of the plurality of subjects.

14. The method according to claim 13, further comprising acquiring monitoring information on monitoring results and monitoring times of the plurality of subjects, wherein the determining operation determines the next subject, and/or the movement path, on a basis of the monitoring information.

15. The method according to claim 13, further comprising acquiring, for each of the plurality of subjects, an unmeasurable period in which the subject is unmeasurable by the detecting wave, and wherein the determining operation determines the next subject, and/or the movement path, so that the unmeasurable period of each of the plurality of subjects falls within a predetermined unmeasurable period.

16. The method according to claim 13, wherein in the measuring operation, biological information of the plurality of subjects is measured; and the determining operation determines the next subject, and/or the movement path, on a basis of the biological information.

17. The method according to claim 13, wherein the detecting wave is an electromagnetic wave.

18. The method according to claim 13, wherein the plurality of subjects exists in the same room.

19. The method according to claim 13, wherein in the measuring, at least two of the plurality of subjects are measured with a common measuring device.

* * * * *